(12) United States Patent
Makeev et al.

(10) Patent No.: US 10,706,262 B2
(45) Date of Patent: Jul. 7, 2020

(54) INTELLIGENT BODY MEASUREMENT

(71) Applicant: 3DLOOK Inc., Wilmington, DE (US)

(72) Inventors: Ivan Makeev, London (GB); Mikhail Orel, Sunnyvale, CA (US); Vyacheslav Shchichko, Mykolayiv (UA)

(73) Assignee: 3DLOOK Inc., Wilmington, DE (US)

( * ) Notice: Subject to any disclaimer, the term of this patent is extended or adjusted under 35 U.S.C. 154(b) by 171 days.

(21) Appl. No.: 15/864,772

(22) Filed: Jan. 8, 2018

(65) Prior Publication Data

US 2019/0213388 A1   Jul. 11, 2019

(51) Int. Cl.
| | | |
|---|---|---|
| G06K 9/00 | (2006.01) | |
| A61B 5/01 | (2006.01) | |
| G06K 9/46 | (2006.01) | |
| G06K 9/66 | (2006.01) | |
| A61B 5/107 | (2006.01) | |
| G06K 9/62 | (2006.01) | |

(52) U.S. Cl.
CPC .......... G06K 9/00201 (2013.01); A61B 5/015 (2013.01); A61B 5/1079 (2013.01); G06K 9/00369 (2013.01); G06K 9/4604 (2013.01); G06K 9/6271 (2013.01); G06K 9/66 (2013.01)

(58) Field of Classification Search
CPC .... G06K 9/00201; G06K 9/6271; G06K 9/66; G06K 9/00369; G06K 9/4604; A61B 5/1079; A61B 5/015; A61B 5/1072; A61B 5/7264; A61B 5/1073

See application file for complete search history.

(56) References Cited

U.S. PATENT DOCUMENTS

| | | | |
|---|---|---|---|
| 7,561,726 B2 | 7/2009 | Lu et al. | |
| 7,876,938 B2 * | 1/2011 | Huang | G06T 7/174 382/128 |
| 8,842,906 B2 | 9/2014 | Watson et al. | |
| 9,189,886 B2 | 11/2015 | Black et al. | |
| 9,292,967 B2 | 3/2016 | Black et al. | |
| 9,489,744 B2 | 11/2016 | Black et al. | |
| 9,526,442 B2 | 12/2016 | Moore et al. | |
| 9,761,060 B2 | 9/2017 | Black et al. | |
| 9,949,697 B2 * | 4/2018 | Iscoe | A61B 5/0077 |
| 2010/0119135 A1 * | 5/2010 | Coupe | G06K 9/32 382/131 |
| 2013/0315470 A1 * | 11/2013 | Watson | G06T 7/75 382/154 |
| 2016/0203361 A1 * | 7/2016 | Black | G06T 7/75 382/203 |
| 2017/0372155 A1 * | 12/2017 | Odry | G06K 9/03 |
| 2019/0035149 A1 * | 1/2019 | Chen | G06T 15/04 |
| 2019/0057515 A1 * | 2/2019 | Teixeira | G06T 7/73 |
| 2019/0057521 A1 * | 2/2019 | Teixeira | G06K 9/6262 |
| 2019/0171871 A1 * | 6/2019 | Zhang | G06K 9/00369 |
| 2019/0318497 A1 * | 10/2019 | Zhao | G06T 7/70 |

\* cited by examiner

*Primary Examiner* — Wesley J Tucker (74) *Attorney, Agent, or Firm* — Gina A. Bibby; Withers Bergman LLP (57) ABSTRACT

A method for estimating the body measurements of a subject from at least two photographic images of the subject. The method includes capturing the photographic images using a digital imaging device, for example, a mobile device camera, and estimating the body measurements of the subject using heatmap data generated by an intelligent computing system such as a trained neural network.

26 Claims, 11 Drawing Sheets

INTELLIGENT BODY MEASUREMENT

TECHNICAL FIELD

Embodiments herein relate generally to a system and method and for estimating the body measurements of a subject, and more specifically, to using photographic images of the subject to estimate the subject's body measurements.

BACKGROUND

Conventional 3D body scanning devices use laser, structured, or white light technologies for body measurement extraction. In addition to being costly and not easily portable, such devices may not provide exact body measurements because the scanned subject is typically clothed and the scanner reconstructs the clothing (not the naked body). Moreover, even when the scanned subject is unclothed, the polygonal (3D) mesh generated by conventional body scanning devices does not provide information about how and where exactly the subject's body measurements should be computed on the reconstructed 3D mesh. Additionally, other body measurement approaches may not generate information with the speed, flexibility and/or accuracy required for use in technology exploitive applications, for example, mobile computing, e-commerce, fast fashion, custom fit apparel, direct-to-consumer apparel production, and the like.

SUMMARY OF INVENTION

Provided herein are systems and methods for estimating the body measurements of a subject using photographs captured from any digital photographic device, particularly mobile phone cameras or other mobile device cameras. The embodiments disclosed herein may include functionality, such as intelligent computing systems (e.g., trained artificial neural networks, and the like) that, among other things, may generate heatmap data and relate the heatmap data to an abstract three-dimensional body model to more accurately and expediently estimate the body measurements of a subject.

BRIEF DESCRIPTION OF THE DRAWINGS

The written disclosure herein describes illustrative embodiments that are non-limiting and non-exhaustive. Reference is made to certain illustrative embodiments that are depicted in the figures, wherein.

DETAILED DESCRIPTION OF ILLUSTRATIVE EMBODIMENTS

A detailed description of the embodiments of the present disclosure is provided below. While several embodiments are described, the disclosure is not limited to any one embodiment, but instead encompasses numerous alternatives, modifications, and equivalents. In addition, while numerous specific details are set forth in the following description to provide a thorough understanding of the embodiments disclosed herein, some embodiments can be practiced without some or all of these details. Moreover, for clarity, certain technical material that is known in the related art has not been described in detail to avoid unnecessarily obscuring the disclosure.

The description may use perspective-based descriptions such as up, down, back, front, top, bottom, and side. Such descriptions are used merely to facilitate the discussion and are not intended to restrict the application of disclosed embodiments.

The description may use the terms "embodiment" or "embodiments," which may each refer to one or more of the same or different embodiments. The terms "comprising," "including," "having," and the like, as used with respect to embodiments, are synonymous, and are generally intended as "open" terms—e.g., the term "includes" should be interpreted as "includes but is not limited to," the term "including" should be interpreted as "including but not limited to," and the term "having" should be interpreted as "having at least."

Regarding the use of any plural and/or singular terms herein, those of skill in the relevant art can translate from the plural to singular and/or from the singular to the plural as is appropriate to the context and/or application. The various singular and/or plural permutations may be expressly set forth herein for the sake of clarity.

The embodiments of the disclosure may be understood by reference to the drawings, wherein like parts may be designated by like numerals. The components of the disclosed embodiments, as generally described and illustrated in the figures herein, could be arranged and designed in a wide variety of different configurations. Thus, the following detailed description of the embodiments of the disclosure is not intended to limit the scope of the disclosure, as claimed, but is merely representative of possible embodiments of the disclosure. In addition, the steps of any method disclosed herein do not necessarily need to be executed in any specific order, or even sequentially, nor need the step be executed only once, unless otherwise specified.

Various embodiments provide systems and methods for estimating the body measurements of a subject using photographs of the subject captured from any digital photographic device, for example, mobile phone cameras or other mobile device cameras. The embodiments disclosed herein estimate the body measurements of a subject without the need for conventional body scanning devices, and with improved accuracy and speed over other body measurement approaches. The body measurements systems and methods disclosed herein may be used in apparel, medical, and health and fitness applications to name a few, or may be used in any other context for which obtaining a subject's body measurements is beneficial. For example, by estimating the body measurements of a subject using photos taken from any digital photographic device, particularly mobile device cameras, companies that sell products where fit is important may more easily and accurately obtain body measurement information. As a result, consumers may make better purchases and companies may reduce the costs associated with returns due to improper fit. Embodiments disclosed herein may also improve the speed and accuracy of estimating body measurements by using, among other things, intelligent computing systems, such as trained artificial neural networks (ANNs). More specifically, because neural networks may be trained on various types of data and their computations may independently become more efficient and accurate over time, the inefficiencies of other body measurement methods may be significantly reduced.

In accordance with various embodiments herein, a system 10 for estimating the body measurements of a subject 12 using two or more photographic images 14 is illustrated with reference to FIG. 1. The photographic images 14 of the subject 12 may be captured using any digital photographic device (e.g., RGB input device), examples include digital cameras, computer cameras, TV cameras, video cameras, mobile phone cameras, and any other mobile device camera. In accordance with embodiments disclosed herein, the subject 12 is not required to assume a particular pose—i.e., the subject's 12 pose may be arbitrary. In various embodiments, the subject 12 may be photographed from different perspectives in any pose. For example, one photograph may include a full-length front profile-view of a subject 12 (FIG. 2A) and another photograph may include a full-length side profile-view of the subject 12 (FIG. 2B). In some embodiments, the photographic images 14 of a subject 12 that are expected to produce meaningful results may contain a single human subject (or other subject) in the foreground and the background may be arbitrary. Additionally, in accordance with embodiments disclosed herein, the subject 12 is not required to be unclothed.

The system 10 may comprise one or more servers 16 that are capable of storing and/or processing, among other things, photographic images 14 of a subject 12, and/or height information 30 associated with the subject 12, which may be used to estimate the body measurements 26 of the subject 12. The one or more servers 16 may be located remotely, such as when coupled via a computer network or cloud-based network, including the Internet, and/or locally, including on the subject's 12 electronic device (e.g., computer, mobile phone or any other portable electronic device). A server 16 may comprise a virtual computer, dedicated physical computing device, shared physical computer or computers, or computer service daemon, for example. A server 16 may comprise one or more processors such as central processing units (CPUs), graphics processing units (GPUs), and/or one or more artificial intelligence (AI) chips, for example. In some embodiments, a server 16 may be a high-performance computing (HPC) server (or any other maximum performance server) capable of accelerated computing, for example, GPU accelerated computing.

The system 10 may comprise one or more intelligent computing systems 18 such as trained artificial neural networks, for example, that may be physically and/or electronically connected to the one more servers 16. In various embodiments, such intelligent computing systems 18 may be trained and learn to do tasks by considering data samples without task-specific programming and may progressively improve their performance over time. The one or more intelligent computing systems 18 may be hardware-based (e.g., physical components) and/or software-based (e.g., computer models). In some embodiments, the one or more intelligent computing systems 18 may be trained to process photographic images 14 of a subject 12 to generate two-dimensional matrices (i.e., probability maps) called heatmaps which, as described with reference to FIG. 3, may be used to estimate a subject's 12 body measurements 26 and/or used to increase the accuracy of such measurements 26. In some embodiments, these heatmaps may comprise landmark 32, contour segment 34, and mask heatmaps 36. A landmark heatmap 32 may comprise two-dimensional probability map that represents the probability that a pixel (or pixels) is associated with a particular part of a photographed subject's 12 body (e.g., elbow, shoulder, hip, leg, and so on). A contour segment heatmap may comprise a two-dimensional probability map that corresponds to a subject's 12 body shape. A mask heatmap 36, may comprise a single two-dimensional probability map indicating the coordinate locations within an image 14 that may correspond to a photographed subject's 12 body or clothing—i.e., the probability that a particular pixel is part of the subject's 12 body or clothing.

In various embodiments, multiple neural networks (or other intelligent computing systems) 18 may be independently trained to process a particular type of photographic image 14. For example, one artificial neural network (or other intelligent computing system) 18 may be trained to process only full-length front-view photographs of a subject 12 while another artificial neural network (or other intelligent computing system) 18 may be trained to process only full-length side-view photographs of a subject 12. In some embodiments, a trained neural network 18 may comprise a fully-convolutional multi-stage recurrent network where each subsequent stage refines the output produced by a previous stage. Alternative intelligent computing systems 18 with unified structure for simultaneously end-to-end processing of different photographic images 14 (e.g., frontal view, side view, and so on) of a subject 12 may also be used consistent with embodiments disclosed herein.

In some embodiments, the system 10 may comprise one or more detectors 20 that may be electronically and/or physically connected to one more servers 16 and one or more intelligent computing systems 18. A detector 20 may be implemented as a software module executed by one or more processors or a hardware module such as application specific integrated circuits (ASICs) or other types of programmable hardware such as gate arrays. As described with reference to FIG. 3, the one or more detectors 20 may be trained to evaluate and/or provide feedback about the quality of the photographic images 14 received by the system 10 based on landmark heatmap 32, contour segment heatmap 34, and mask heatmap 36 data generated by the one or more intelligent computing systems 18. In some embodiments, such feedback may be provided to a user of the system 10, the photographed subject 12, and/or the like, to strengthen (i.e., improve the accuracy of) the body measurement estimates 26 of a subject 12 output by the system 10. In some embodiments, multiple detectors 20 may each be independently trained to evaluate and/or provide feedback about a particular type or types of photographic images 14. For example, one detector 20 may be trained on datasets of full-length front-view photographic images 14 while another detector 20 may be trained on datasets of full-length side profile-view photographic images 14.

The system 10 may comprise a three-dimensional (3D) model matching module 22 that may be electronically and/or physically connected to the one or more servers 16 and the one or more intelligent computing systems 18. In some embodiments, as described with reference to FIG. 3, the 3D model matching module 22 may estimate the body measurements 26 of a photographed subject 12 using the height 30 of the photographed subject 12 and landmark heatmaps 32 generated by the one or more intelligent computing systems 18. The 3D model matching module 22 may be implemented as a software module executed by one or more processors or a hardware module such as application specific integrated circuits (ASICs) or other types of programmable hardware such as gate arrays. In various embodiments, the body measurement estimates 26 generated by the 3D module matching module 22 may comprise: chest volume, waist volume, hip volume, front shoulder width, front chest width, front waist width, front hip width, shoulder to waist length, sleeve length, body length, leg length, outside leg length, inside leg length, and so on.

Figure 1:
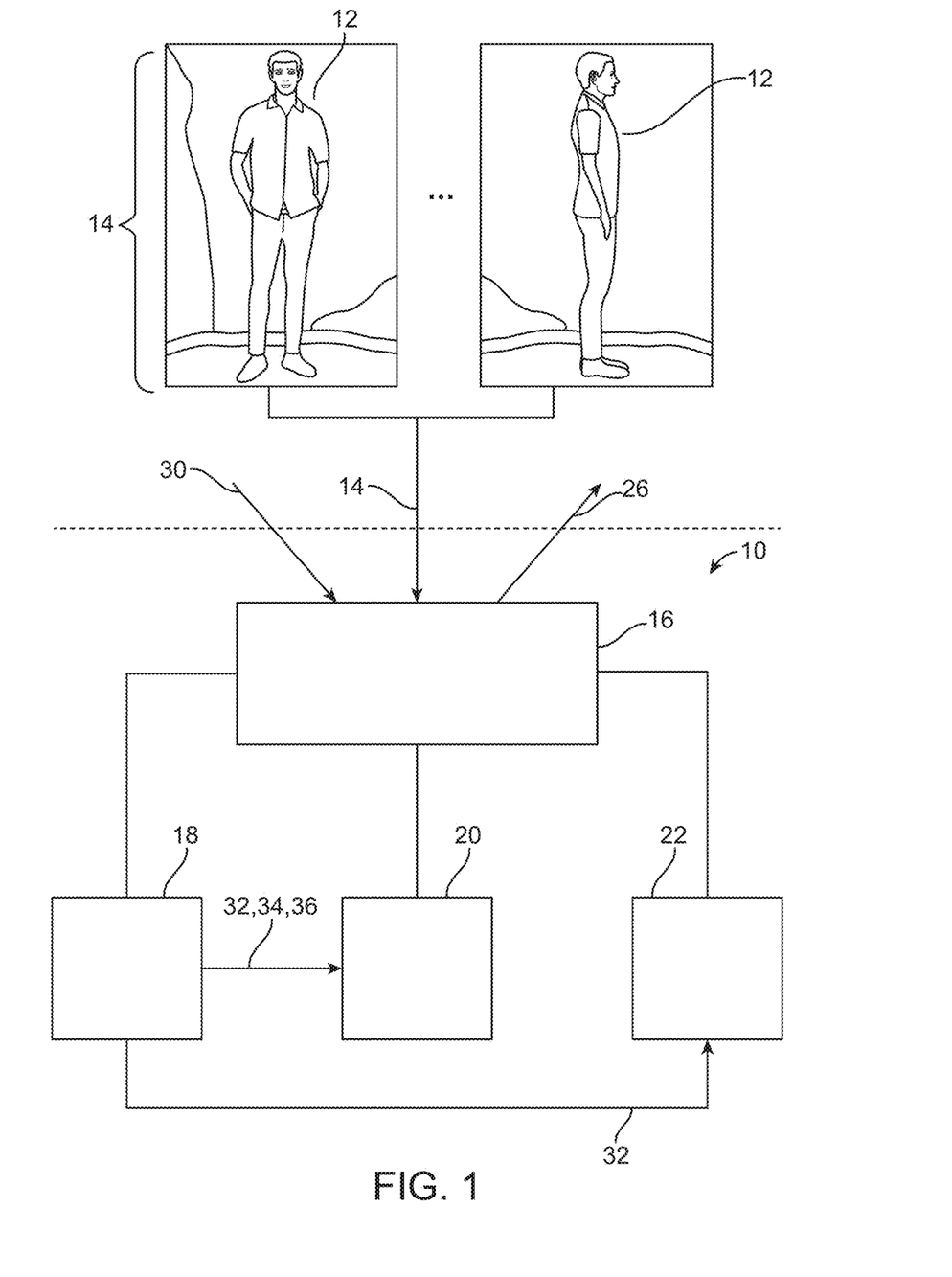
FIG. 1 illustrates a simplified block diagram of a system for estimating the body measurements of a subject consistent with embodiments of the present disclosure.
Figure 2A:
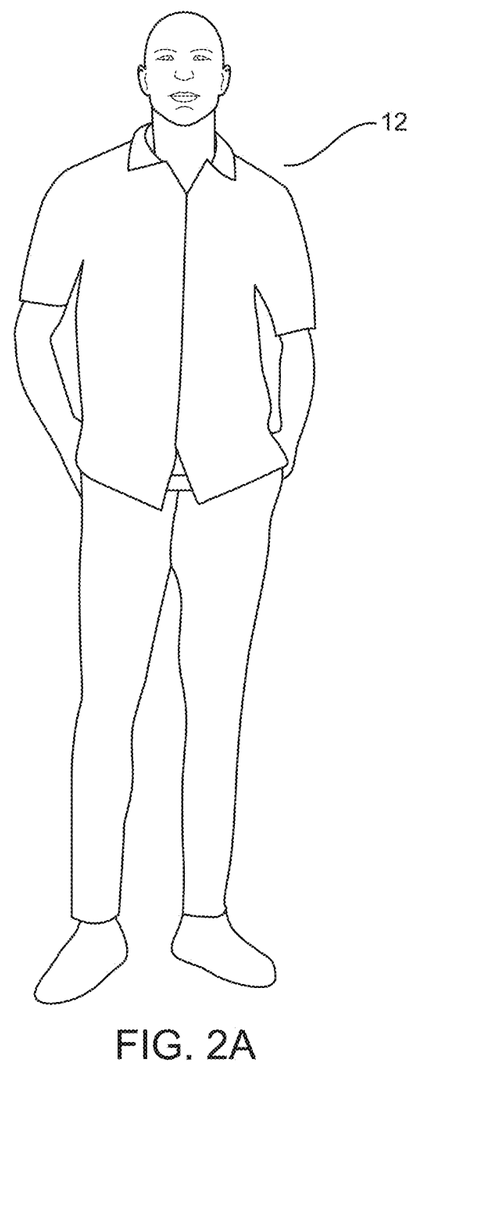
FIG. 2A illustrates a simplified full-length front-view of a human subject consistent with embodiments of the present disclosure.
Figure 2B:
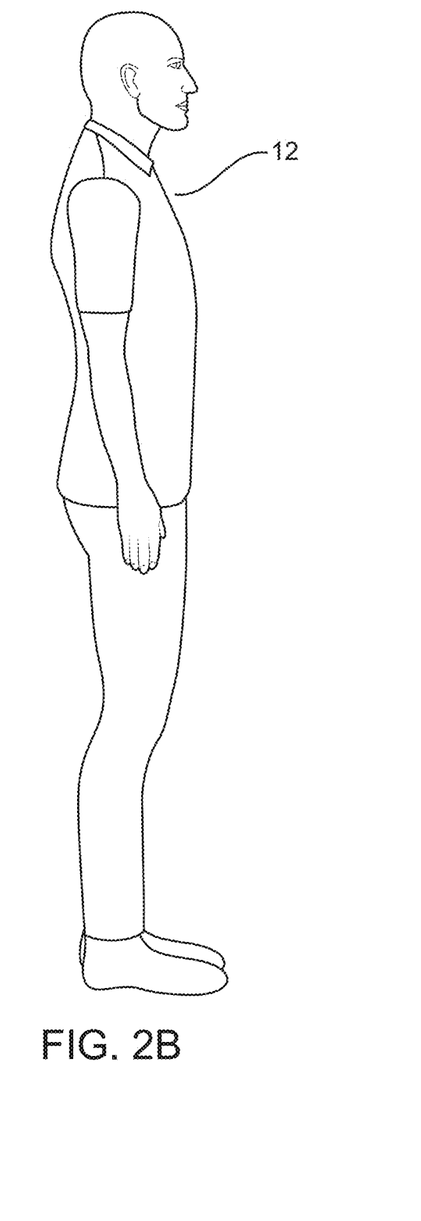
FIG. 2B illustrates a simplified full-length side-view of a human subject consistent with embodiments of the present disclosure.

The functions of single modules or units of the system 10 shown in FIG. 1 may be separated into multiple units or modules, or the functions of multiple modules or units may be combined into a single module or unit. The functions of single modules or units of system 10 may be implemented as a software module executed by one or more processors or a hardware module such as application specific integrated circuits (ASICs) and/or other types of programmable hardware such as gate arrays.

The system 10 (or portions thereof) may be integrated with websites, mobile applications, fashion and apparel systems, medical systems, health and fitness systems, conventional 3D body scanning systems (e.g., to provide the locations of certain parts of a photographed subject's 12 body that may then be mapped to a scanned 3D mesh generated by the conventional 3D body scanning systems), or any other system where obtaining the body measurements 26 of a subject 12 using photographic images 14 is desired. For example, the system 10 (or portions thereof) may be integrated with an apparel company's website to facilitate apparel fit. In particular, the system 10 (or portions thereof) may be integrated with a company's website where photographic images of a customer are received by the system 10 via the company's website, the customer's body measurements estimated by the system 10, and the estimated body measurements used by the company to select appropriately sized articles of clothing for the customer using, for example, the company's product fit/size chart data. In other examples, the system 10 may be implemented as a mobile application on the subject's 12 mobile phone. Still other examples are possible.

In accordance with various embodiments herein, and with reference to FIG. 1, a method for estimating the body measurements of a subject 12 using two or more photographic images 14 is illustrated with reference to FIG. 3. Two or more photographic images 14 of a subject 12 may be received and stored on one or more servers 16. In various embodiments, the height 30 of the subject 12 may also be received and stored on the one or more servers 16. The photographic images 14 may be captured using any digital photographic device, including digital cameras, mobile phone or other mobile device cameras. And the subject 12 may be photographed in any pose, and from any perspective (e.g., front-view, side-view, perspective-view, and so on). For example, in some embodiments, one photograph 14a may be a full-length front-view image of a subject 12 and another photograph 14b may be a full-length side-view image 14b of the subject 12.

The one or more photographic images 14 of the subject 12 stored on one or more servers 16 may be received by one or more intelligent computing systems, such as previously trained neural networks 18. The one or more neural networks 18 may be trained and learn to do tasks by considering data samples without task-specific programming; over time, as the one or more neural networks 18 consider additional data samples they may progressively improve their performance. For example, in some embodiments, one neural network 18a may be trained to generate 2D matrices (i.e., probability maps) called heatmaps using one or more datasets of full-length front-view images (e.g., a few thousand images) of various subjects, while another neural network 18b may be trained to generate heatmaps using one or more datasets of full-length side-view images of various subjects. In some embodiments, landmark heatmap data 32 may be used by a 3D model matching module 22 to generate the body measurements estimates 26 of a subject 12. In some embodiments, a trained neural network (or other intelligent computing system) 18 may be trained to generate heatmap output values that may fall into [0, 1] interval. Heatmap data generated by a neural network (or any other intelligent computing system) 18 may comprise landmark heatmaps 32, contour segment heatmaps 34, and mask heatmaps 36. In some embodiments, the landmark heatmap 32, contour segment heatmap 34, and mask heatmap 36 data may be used by a detector 20 to generate feedback about the quality of photographic images 14 of the subject 12 to improve the accuracy of the subject's 12 body measurement estimates 26.

In some embodiments, a trained neural network (or any other intelligent computing system) 18 may generate a landmark heatmap 32, $H_i(x,y)$, by computing two-dimensional (2D) probability map distributions using a photographic image 14 containing the subject 12. For example, trained neural network 18a may generate a landmark heatmap 32a by computing two-dimensional (2D) probability map distributions using a full-length front-view photographic image 14a containing the subject 12. Similarly, trained neural network 18b may generate a landmark heatmap 32b by computing two-dimensional (2D) probability map distributions using a full-length side-view photographic image 14b containing the subject 12. These two-dimensional probability map distributions may represent the probability that a pixel (or pixels) is associated with a particular part of the photographed subject's 12 body (e.g., elbow, shoulder, hip, leg, and so on). From the two-dimensional probability map distributions, neural networks 18a, 18b may calculate the two-dimensional coordinate values ($x_i$, $y_i$) 104 in image space (i.e., pixels) for keypoint i using the formula:

$$x_i, y_i = \mathrm{argmax}(H_i),$$

where, $H_i$ is the corresponding two-dimensional probability map of i-th keypoint. In particular, landmark heatmaps 32 generated by a trained neural network 18 (or any other intelligent computing system) may indicate the areas (referred to herein as two-dimensional (2D) keypoints (or keypoint pairs) 104 in an input image 14 where a particular part of the photographed subject's 12 body (e.g., elbow, chest, shoulder, hip, leg, and so on) could be located (FIG. 4). Through the mechanism of neural network training, the one or more neural networks (or other intelligent computing systems) 18 may be trained to generate landmark heatmaps 32 using one or more datasets of images where, for each image contained in a dataset, the location of a different part of the body has previously been identified. As a result of such training, the less the $2^{nd}$ centralized and normalized momentums (M02/M00 and M20/M00) of each landmark heatmap 32 (i.e., the less the spread), the more precise the localization of each location of a different part of the body.

Figure 5:
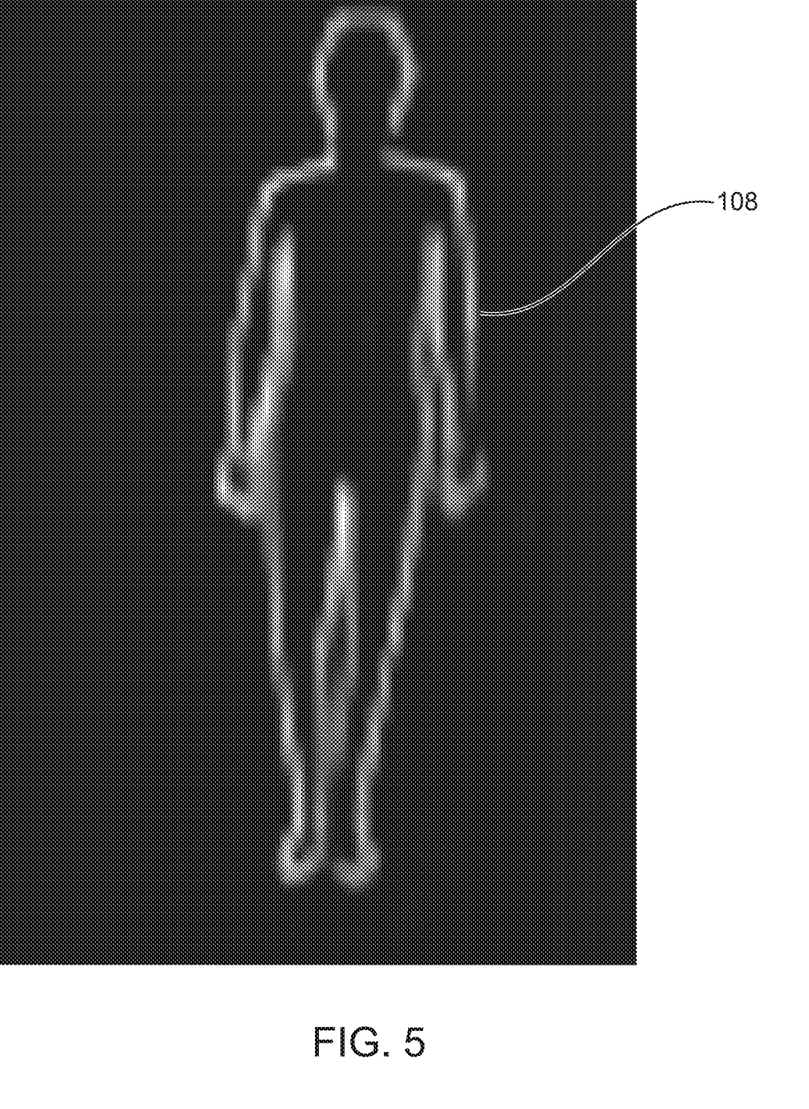
FIG. 5 illustrates an exemplary two-dimensional contour segment combined as a single probability map consistent with embodiments of the present disclosure.

In some embodiments, a trained neural network (or any other intelligent computing system) 18 may generate a contour segment heatmap 34, $S(x,y)$, by: (i) generating 2D contour segments 106, where each contour segment 106 represents an area connecting neighboring keypoint pairs 104 (FIG. 4), and (ii) combining contour segments 106 to form a single probability map 108 (FIG. 5) that estimates the body shape of the subject 12 by connecting one 2D keypoint pair 104 to the next neighboring 2D keypoint pair 104, and so on, until the last keypoint pair 104 in the sequence is connected to the first keypoint pair 104 in the sequence. For example, this may be done using the formula:

$$S(x, y) = \max_i S_i(x, y),$$

where $S(x,y)$ is the single probability map (i.e., contour segment heatmap 34) corresponding to the subject's 12 body shape for 2D keypoint pairs (x,y) 104. For example, with reference to FIG. 3, trained neural network 18a may independently generate a two-dimensional contour segment heatmap 34a from a full-length front-view photographic image 14a of the subject 12. Similarly, neural network 18b may independently generate two-dimensional contour segment heatmap 34 from a full-length side-view photographic image 14b of the subject 12. In various embodiments, in addition to outputting the segment heatmap data 34 to a detector 20, the segment heatmap data 34 may be used internally by a neural network 18 to strengthen connections between the 2D coordinates ($x_i$, $y_i$) computed from the landmark heatmaps 32.

Through the mechanism of neural network training, the higher the value of a contour segment heatmap 34 in the areas corresponding to keypoint pairs 104 that a contour segment 106 connects, the higher the quality of the segment localization. Additionally, in some embodiments, the higher the extent of a contour segment heatmap 34, where extent is defined as a ratio of the higher and lower eigenvalues of the covariance matrix of each contour segment heatmap 34, the better the quality of each contour segment 106. This is because each contour segment 106 may ideally be a line 1 element wide.

Figure 6:
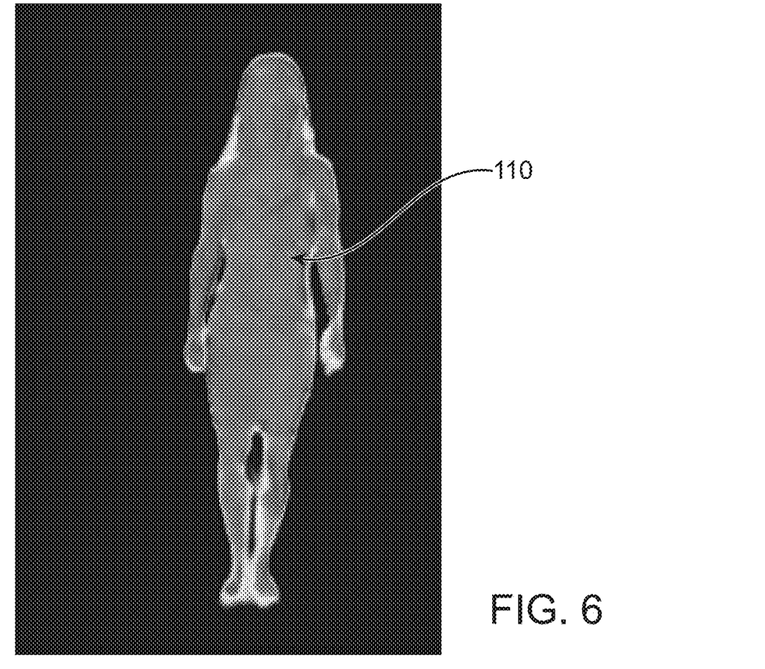
FIG. 6 illustrates an exemplary raw full-body two-dimensional mask consistent with embodiments of the present disclosure.
Figure 7:
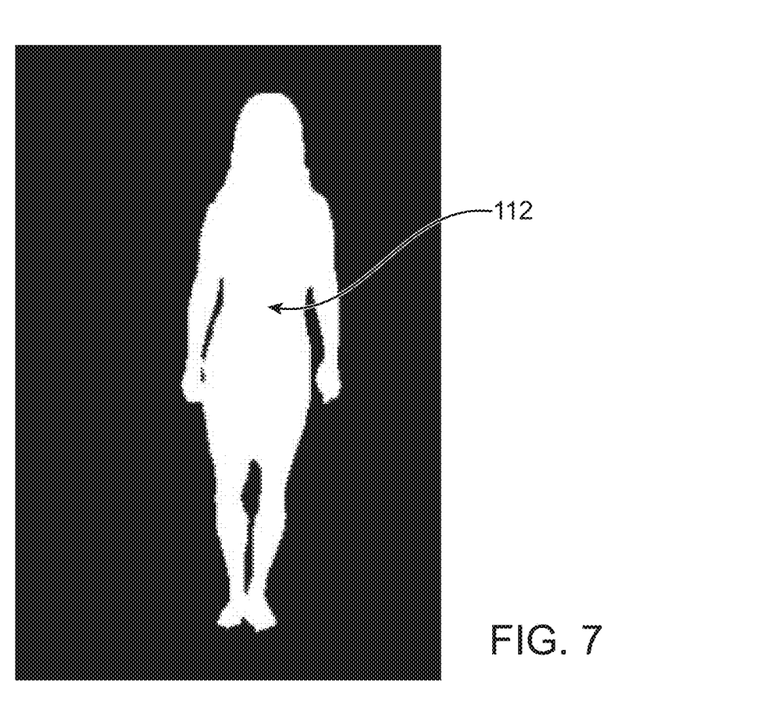
FIG. 7 illustrates an exemplary post-processed full-body two-dimensional mask consistent with embodiments of the present disclosure.

In some embodiments, a trained neural network 18 (or any other intelligent computing system) may generate a mask heatmap 36, where M(x,y) is a single probability map indicating the coordinate locations (x, y) 104 within an image 14 that may correspond to a photographed subject's 12 body or clothing—i.e., the probability that a particular pixel is part of the subject's 12 body or clothing. For example, with reference to FIG. 3, trained neural network 18a may independently generate a two-dimensional mask heatmap 36a from a full-length front-view photographic image 14a of the subject 12. Similarly, neural network 18b may independently generate two-dimensional mask heatmap 36b from a full-length side-view photographic image 14b of the subject 12. In accordance with various embodiments disclosed herein, FIGS. 6 and 7 illustrate exemplary raw (unprocessed) 110 and processed 112 body mask heatmaps 36, respectively.

Figure 8:
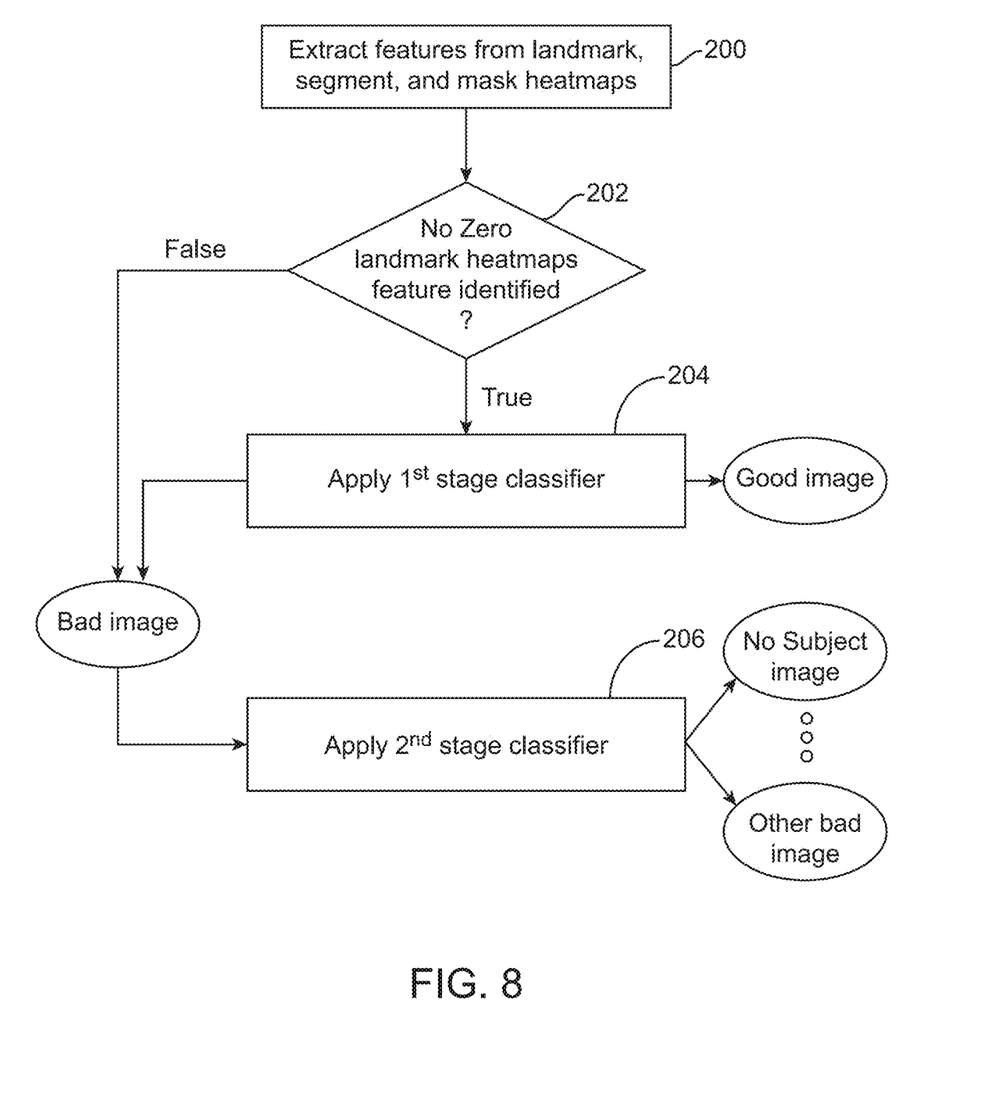
FIG. 8 illustrates a simplified process flow relating to classifying photographic images consistent with embodiments of the present disclosure.

In some embodiments, with reference to FIG. 8, the landmark 32, segment 34, and body mask 36 heatmaps generated by an intelligent computing system 18, such as a trained neural network, may be received by a detector 20. At 200, the detector 20 may extract features from the landmark 32, segment 34, and body mask 36 heatmaps to classify images 14 as Good or Bad. These features may be related to how close an input image 14 is to images used during the neural network training, for example. Features extracted from the landmark heatmaps 32 by a detector 20 may comprise: number of zero landmarks, landmark spread, and landmark mar. The number of zero landmarks may be defined as the number of landmark heatmaps 32 whose maximum is less than a certain value (e.g., a low multiple of a precision limit of float 32). The landmark spread may be defined as the square root of the sum of squares of the second moments along axes (M02/M00 and M20/M00), averaged over all landmark heatmaps 32. The landmark max may be defined as the maximum of each landmark heatmap 32, averaged over all landmark heatmaps 32.

Features extracted from the segment heatmaps 34 by the detector 20 may comprise: segment quality, segment mar, segment poles, and number of zero segments. Segment quality may be defined as the ratio of the higher and lower eigenvalues of the covariance matrix of each segment heatmap 34, summed over all segment heatmaps 34, and weighted by the distance between keypoints 104 defining the segment. Segment max may be defined as the max of the segment heatmap 34, averaged over all segment heatmaps 34. Segment poles may be defined as the values of the segment heatmap 34 at the location of its keypoints 104 (subsampled to the segment heatmap resolution), and averaged over all segment heatmaps 34. The number of zero segments may be defined as the number of segment heatmaps 34 whose maximum is less than a certain value (e.g., a low multiple of the precision limit of float 32).

Features extracted from the mask heatmaps 36 by the detector 20 may comprise mask quality. Mask quality may be defined as the ratio of mask heatmap slice areas, as sliced at levels of approximately 0.7 and 0.35, respectively.

In some embodiments, the closer an image 14 is to image training sets, the higher the values of the extracted landmark max, segment quality, segment max, segment poles, and mask quality features, and the lower the values of the extracted number of zero landmarks, landmark spread, and number of zero segment features.

Once the heatmap features are extracted by the detector 20, the detector 20 may process a photographic image 14 in one or more stages to generate information about whether the image 14 of a subject 12 satisfies certain pre-defined criteria. For example, at 202, a detector 20 may determine whether there are no zero landmarks associated with a photographic image 14. If false (i.e., there is at least one zero landmark associated with an image 14), then the image 14 may be classified by the detector 20 as Bad and passed downstream for further processing at a subsequent classifier stage 206. If true (i.e., there is no zero landmark heatmap 34 associated with the image 14), then the image 14 may be passed downstream for further processing at a subsequent classifier stage 204.

All of the features extracted from the landmark 32, segment 34, and mask 36 heatmaps are then combined into a classifier that considers each of the extracted features to be distributed normally, and independent of each other, at 204. For example, the classifier may be a Gaussian Naïve Bayes Classifier (or equivalent classifier):

$$p(X \mid C_j) \propto \prod_{k=1}^{d} p(x_k \mid C_i)$$

where X is $\{x_i\}$, i=1 ... k (vector features), $p(X|C_j)$ is the probability of a given feature vector provided that is belongs to class $C_j$, and $$p(C_j \mid X) \propto p(C_j) \prod_{k=1}^{d} p(x_k \mid C_j),$$

where $p(C_j|X)$ is the posterior probability of class membership. The classifier applied at stage 204 may be any classifier that considers each of the extracted features to be distributed normally, and independent of each other.

The detector 20 may then separate images 14 into Good and Bad at 204. For example, the detector 20 may classify a Good image 14 as one that satisfies the following criteria: (i) the Euclidian distance between the first centralized and normalized momentums of landmark heatmaps 32 by axes X and Y (M01/M00 and M10/M00) and the ground truth of the corresponding two-dimensional keypoint 104 is less than a pre-defined value D, where D may range from approximately 3 to 6; and (ii) the area of the mask heatmap 36 is approximately at level 0.5 and the area of the ground truth mask differ by less than a pre-defined number of pixels M, where M may range from approximately 5% to 10% of the area of the ground truth mask. Images that do not meet these criteria may be classified by the detector 20 as Bad and passed to stage 206.

The detector 20 may further classify each Bad image 14 by applying a classifier at 206. Here again, all of the features extracted from the landmark 32, segment 34, and mask 36 heatmaps may be combined into a classifier, such as a Gaussian Naïve Bayes Classifier, that considers each of the extracted features to be distributed normally, and independent of each other. These further classifications of Bad images may represent any image 14 that is not currently included in a neural network's 18 training set. For example, the detector 20 may classify a Bad image as NoSubject due to the absence of a subject 12 in an image 14, and so on. Over time, as additional data is collected, and the one or more intelligent computing systems 18 are trained on the data, images 14 that were once classified or subclassified as Bad may become Good.

Feedback about the quality of images 14 that is generated by a detector 20 may be used to increase the accuracy of the subject's 12 body measurements 26. In some embodiments, such feedback may be output to a user of the system 10 (FIG. 1), the photographed subject 12, and/or the like.

Figure 3:
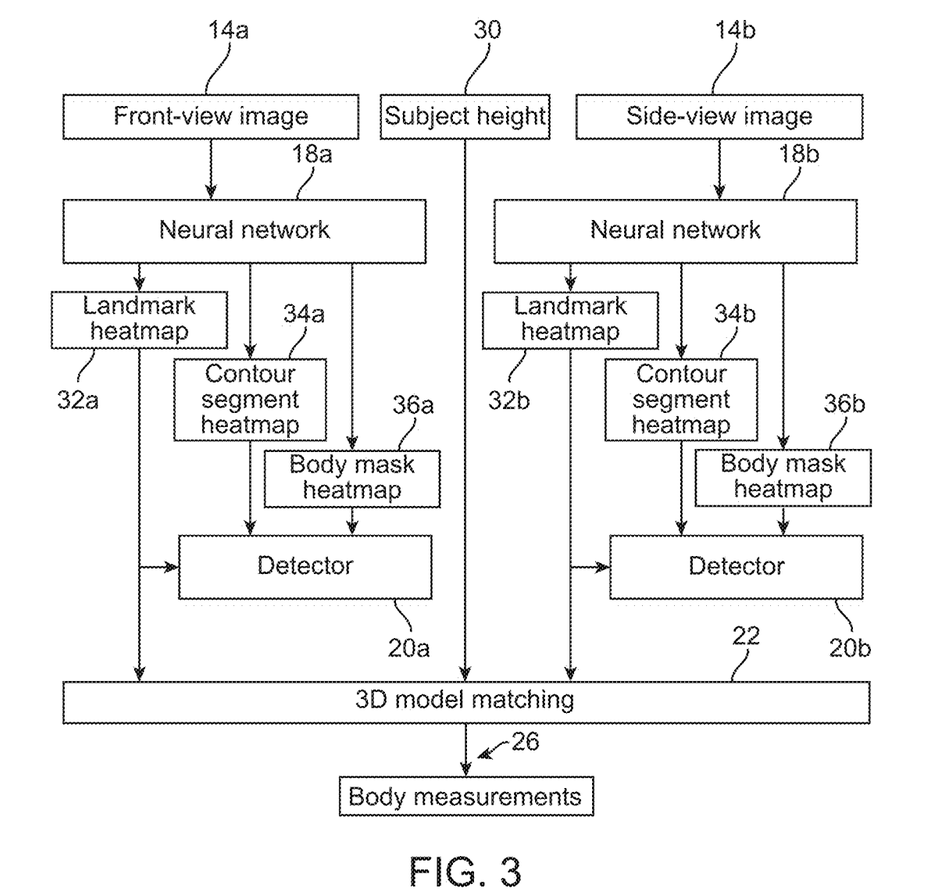
FIG. 3 illustrates a simplified process flow for estimating the body measurement of a subject consistent with embodiments of the present disclosure.
Figure 4:
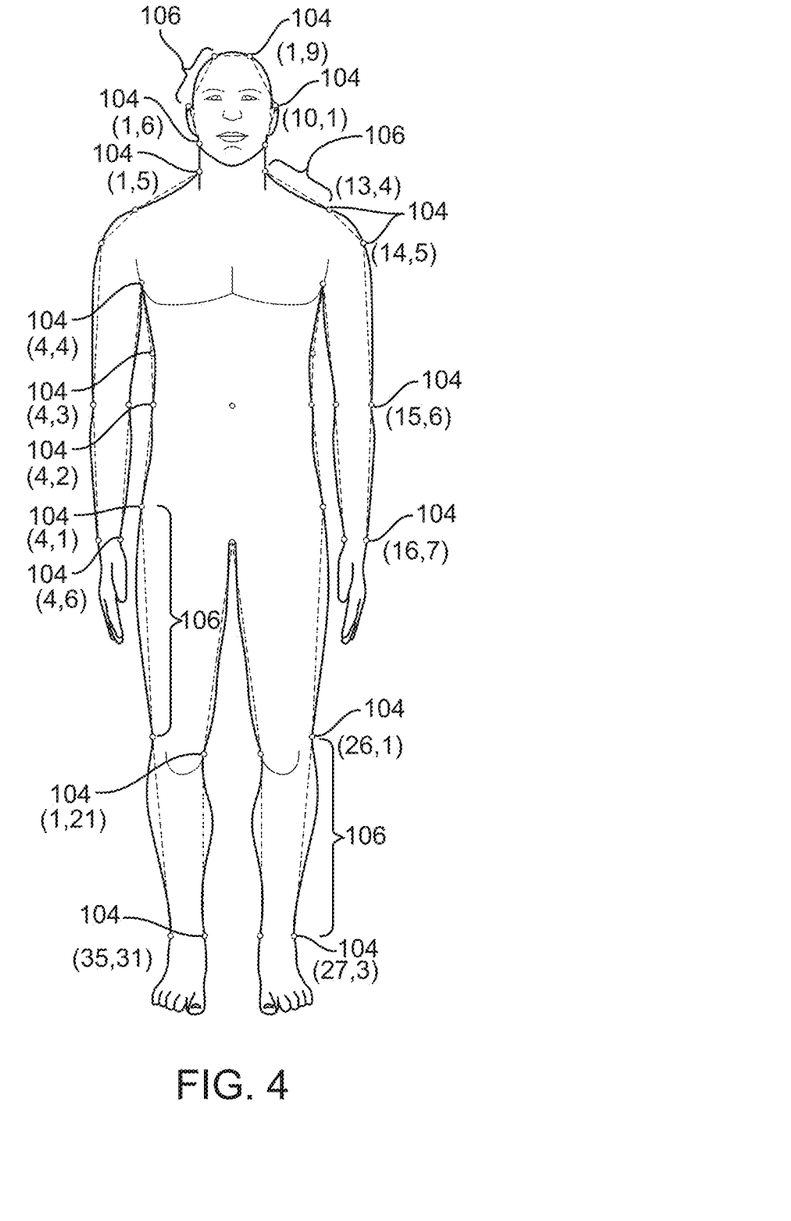
FIG. 4 illustrates keypoint coordinates and contour segments associated with various body parts of a human subject consistent with embodiments of the present disclosure.
Figure 11A:
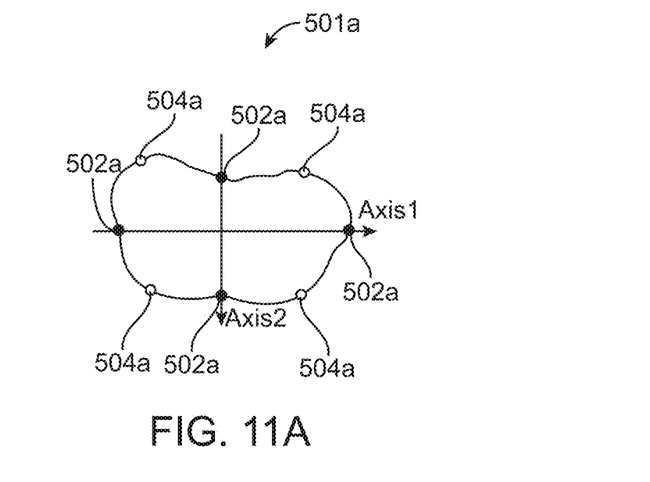
FIG. 11A illustrates an exemplary contour point set consistent with embodiments of the present disclosure.
Figure 11B:
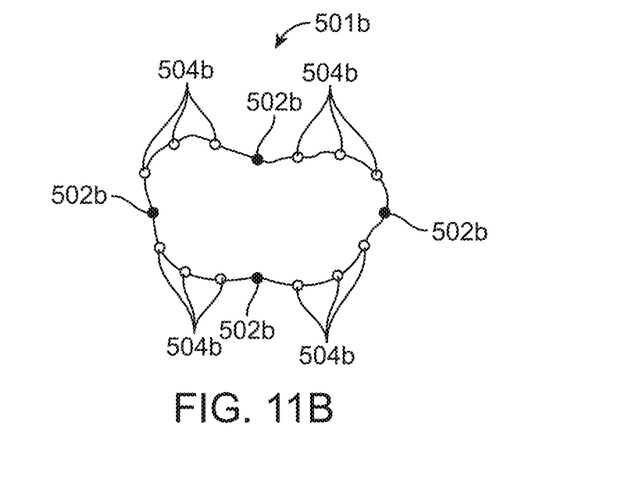
FIG. 11B illustrates an exemplary contour point set consistent with embodiments of the present disclosure.
Figure 11C:
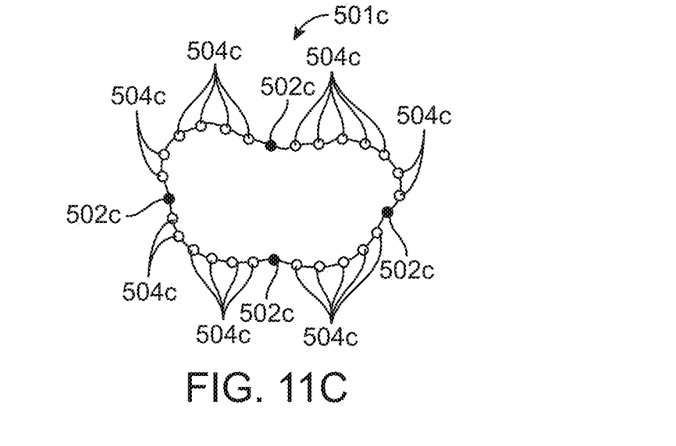
FIG. 11C illustrates an exemplary contour point set consistent with embodiments of the present disclosure.

In some embodiments, with reference to FIG. 3, a three-dimensional (3D) model matching module 22 may estimate the body measurements 26 of a photographed subject 12. In general, the two-dimensional coordinates $(x_i, y_i)$ 104 generated by a trained neural network 18 from landmark heatmap data 32 may be used to generate a two-dimensional contour model using parameterized projections of an abstract 3D body model 300 (FIG. 9) onto an image plane using a virtual camera—i.e., the proportions of an abstract 3D body model 300 (e.g., 3D model of a human body or any other relevant body) may be adjusted based on the 2D coordinate data 104 generated by the trained neural network 18. More specifically, with reference to FIG. 9, using a human subject 12, for example, the 3D model matching module 22 may create an abstract human body spline model 300 (as a set of cross-sections) using a contour point set 501 (FIG. 11) that is extracted from the landmark heatmaps 32 output from one or more neural networks 18. In some embodiments, a contour point set 501 may comprise main control points 502, which may be used for radial basis function (RBF) curve updates, and additional control points 504 that may be spawned equidistantly. For example, with reference to FIG. 11A, contour point set 501a may comprise main control points 502a and additional control points 504a. In a further example, with reference to FIG. 11B, contour point set 501b may comprise main control points 502b and additional control points 504b. In yet another example, with reference to FIG. 11C, contour point set 501c may comprise main control points 502c and additional control points 504c.

Figure 9:
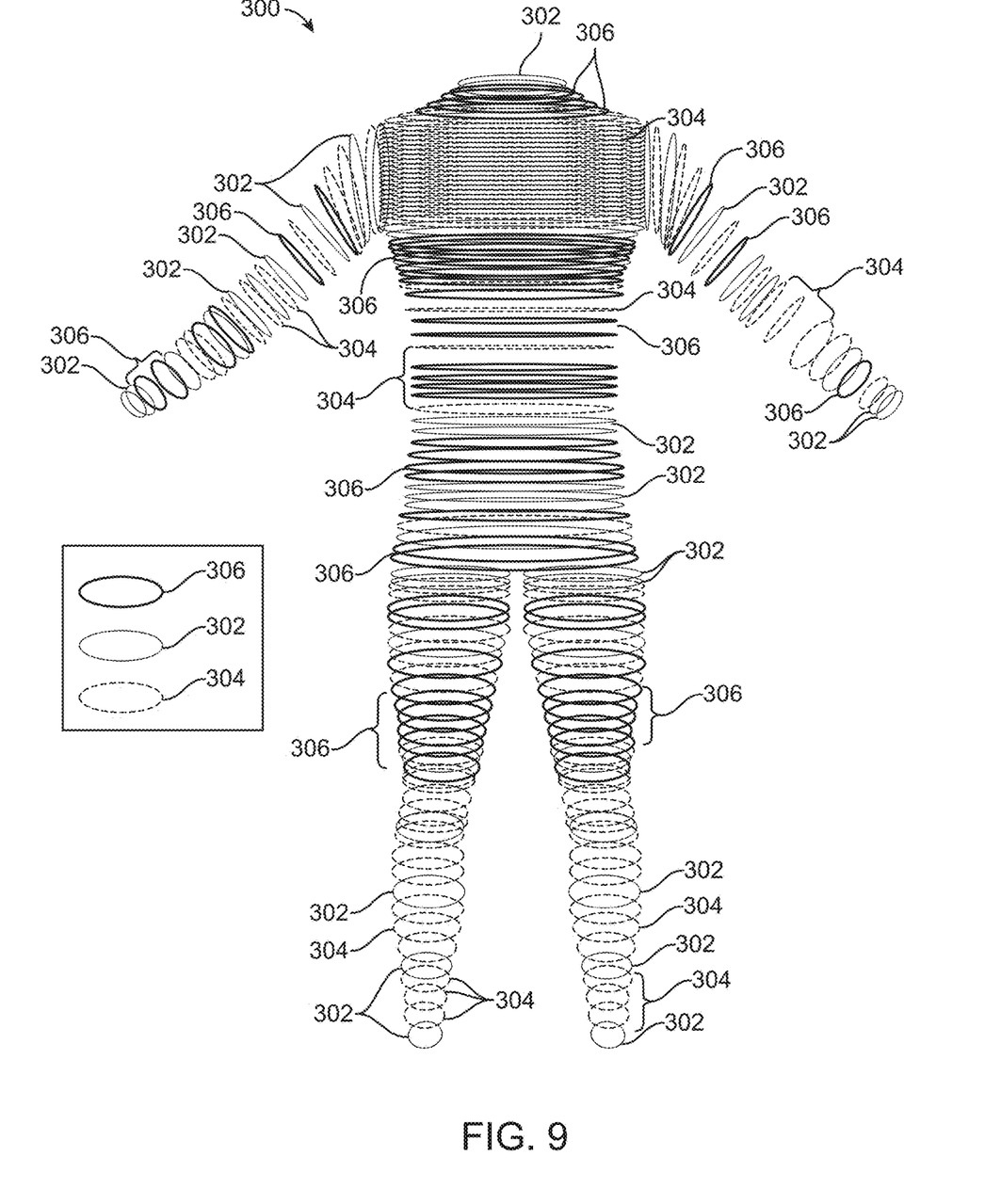
FIG. 9 illustrates an exemplary abstract human body shape spline model consistent with embodiments of the present disclosure.

The abstract human body spline model 300 (FIG. 9) is a set of body "slices" 302, 304, 306 approximated by with B-spline curves (also known as Spline functions). The shapes of the body "slices" 302, 304, 306 may be controlled by curve control points 502, 504 (FIG. 11) that may perform modifications of a cross-section (i.e., body "slice"). Spline functions may be constructed by the 3D model matching module 22 as linear combinations of B-splines with a set of control points:

$$C(t) = \Sigma_{i=0}^{n} N_{i,p}(t) \cdot (P_i)$$

where basis functions may be described using the Cox-de Boor recursion formula:

$$N_{i,0}(t) = \begin{cases} 1, & t_i \leq t \leq t_{i+1} \\ 0, & \text{in other case} \end{cases}$$

$$N_{i,j}(t) = \frac{t - t_i}{t_{i+j} - t_i} \cdot N_{i,j-1}(t) + \frac{t_{i+j+1} - t}{t_{i+j+1} - t_{i+1}} \cdot N_{i+j+1(t)}; \quad j = 1, p.$$

In some embodiments, with reference to FIG. 9, the major slices 302 of exemplary human a body shape spline model 300 may describe the primary human body measurements. And the slices 304 and slices 306 may define various body regions (e.g., crotch to waist, waist to thorax, thorax to chest, etc.). Each region is controlled by a different set of major cross-sections 302, and each cross section 302 represents the primary anthropometric measurements of the human body that influence body shape during the shape evaluation and deformation process.

Figure 10A:
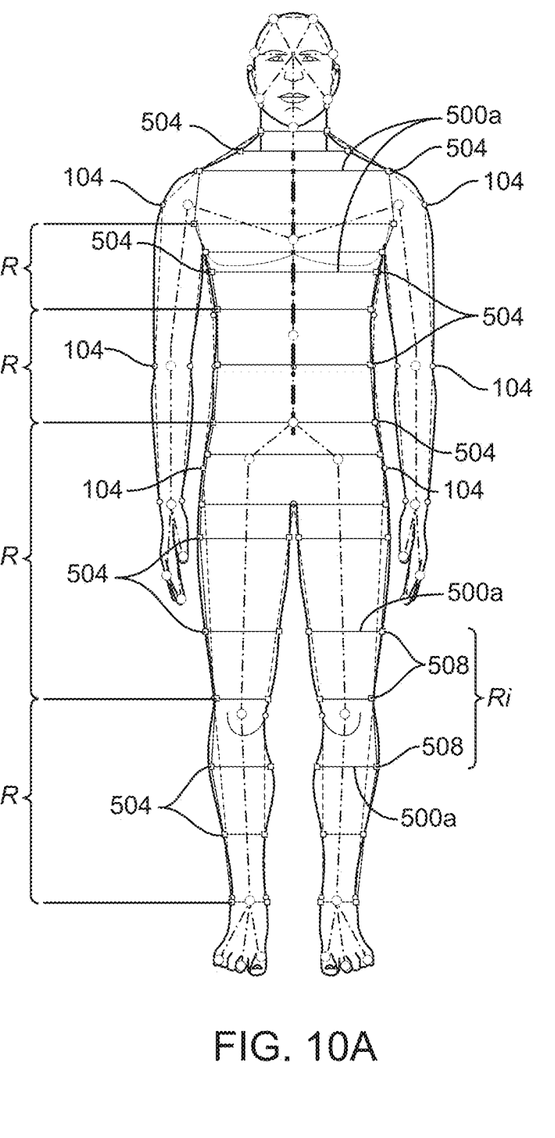
FIG. 10A illustrates exemplary model cross sections with two-dimension image landmark and main linear cross-section values in a frontal projection consistent with embodiments of the present disclosure.
Figure 10B:
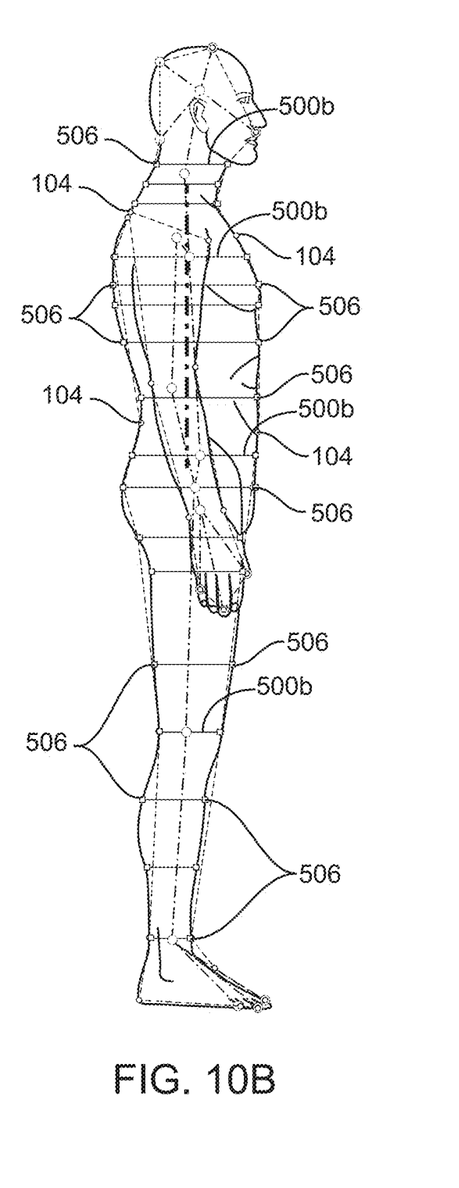
FIG. 10B illustrates exemplary model cross sections with two-dimension image landmark and main linear cross-section values in a side projection consistent with embodiments of the present disclosure.

In some embodiments, with reference to FIGS. 10A (front) and 10B (side), using the two-dimensional keypoint 104 coordinates ($x_i$, $y_i$)—where, as previously discussed, $x_i$, $y_i$=argmax($H_i$) and $H_i$ is the corresponding two-dimensional probability map of i-th keypoint—the 3D model matching module 22 may project major human body model cross-sections 302 (FIG. 9) as two-dimensional images. The 3D model matching module 22 may use the height 30 of a subject 12 to proportionally align the scale of a 3D model 300 relative to the virtual camera that is used for the projection. The 3D model matching module 22 may then compute main linear cross-section values 500 in frontal and side projections (FIGS. 10A and 10B) by matching the main four control points 502 (FIG. 11) in frontal projections 504 (FIG. 10A) and side projections 506 (FIG. 10B) projections with corresponding 2D landmarks 104. The main cross-section control points 502 (FIG. 11) are used for the curves construction using B-splines that define deformation of a corresponding body region R (FIG. 10A).

Figure 12:
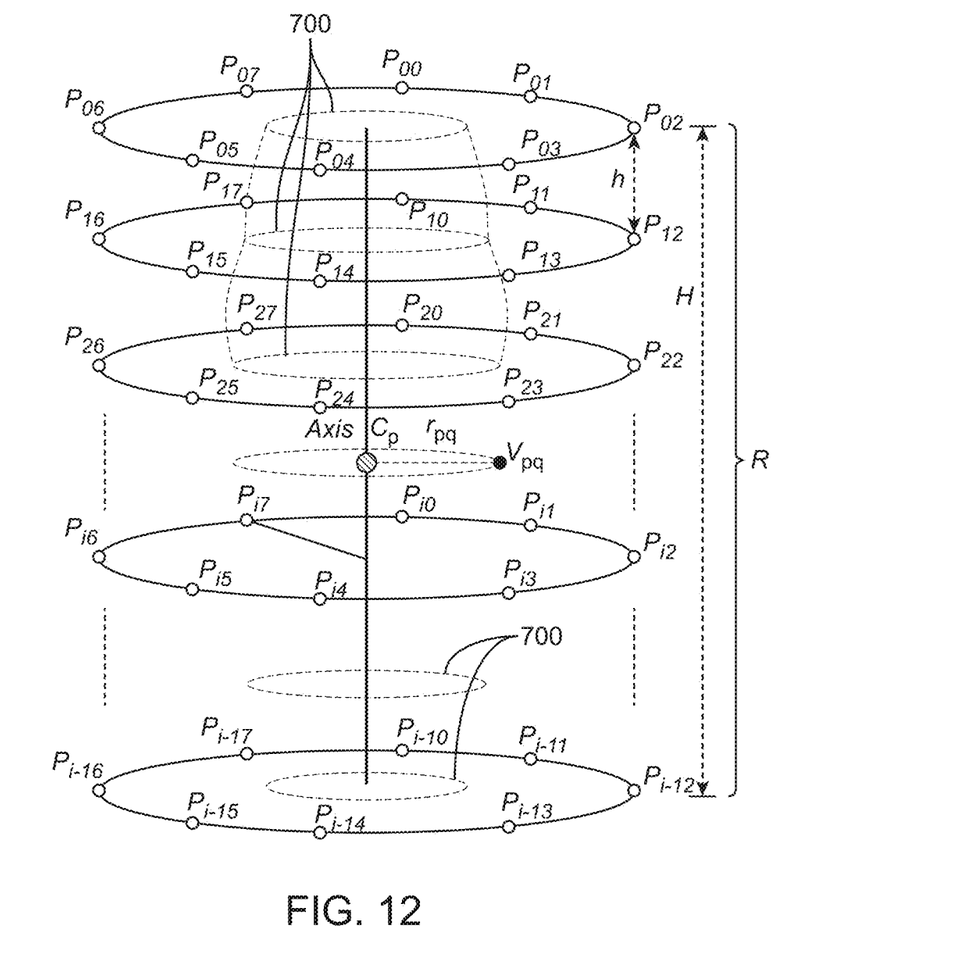
FIG. 12 illustrates a regional deformation (with radius free form deformation) consistent with embodiments of the present disclosure.

One or more main cross sections 700 (FIG. 12) may influence neighboring regions Ri (FIG. 10A) and their corresponding cross-section curves 508 (FIG. 10A), as described below. Then deformation of the remaining curves will be conditioned on the main regions R (FIG. 10A). For example, in some embodiments, once the main linear cross-section values are computed, the 3D model matching module 22 may compute regional and radius distance free deformations of the cross-sections 700 (FIG. 12). In particular, the 3D model matching module 22 may approximate cross-section curves and interpolate the curves of other regions between the closest main curves. With reference to FIG. 12, by using a constraint region (rather than a constraint point) and a different type and variable number deformation for each region R (see also FIG. 10A), the 3D model matching module 22 may use "Regional Deformation (with Radius Distance Free Form Deformation)" method (or similar methods) to compute the regional and radius distance free deformations using the formula:

$$d(v_i)=d_i=v_i+\Sigma_{j=1}^{k} s_j n_i f_i(L(v_i)),$$

where $d(\cdot)$ is the deformation function $R^3 \rightarrow R^3$, k is the number of deformation functions that will be applied on M where M is the set of 3D vertices of the cross-section curve; $d_i$ is the new position of $v_i$ after deformation; $n_i$ is the normal vector of $v_i$, which is not changed after deformation because the deformation is in the same direction as the normal; and $s_j$ is the scale factor of the j-th deformation function. L is the normalized local coordinate function, L: $R^3 \rightarrow R^3$, $0 \leq L_i(\cdot) \leq 1$, i=1, 2, 3:

$$L(v_i) = \left( \frac{v_{i,1} - X_{min,1}}{X_{max,1} - X_{min,1}}, \frac{v_{i,2} - X_{min,2}}{X_{max,2} - X_{min,2}}, \frac{v_{i,3} - X_{min,3}}{X_{max,3} - X_{min,3}} \right).$$

In various embodiments, the 3D model matching module 22 may generate a mesh that approximates a geometric domain of a photographed subject's 12 body. The mesh may be a polygonal mesh or other any other appropriate mesh shape. For human subjects, in particular, various methods may be adopted for creating surfaces and contours of the human body because the shape of each human part is cylinder-like. In some embodiments, one such mesh generation method may comprise extracting vertices from the contour curve of cross-sections, and then creating surfaces from the contours. In some embodiments, by controlling the interval between two neighboring vertices on a cross-section, multi-resolution vertices may be generated on the cross-section, which makes it easier to construct a multi-resolution mesh for a human model surface.

In some embodiments, after obtaining the vertices on contour curves, the surface of each part of a human body may be constructed using, for example, a Meyer's "Surface from Contours" method, or other similar methods. See, e.g., David Meyers, Shelley Skinner, and Kenneth Sloan, *Surfaces from Contours*, 11 ACM Transactions on Graphics, Issue 3, 228-258 (July 1992). Following the human body shape deformation process, estimated body measurements 26 of the subject 12 may be calculated from updated B-Spline lengths by computing the perimeter of the entire cross-section curve, using curvilinear integral as follows:

$$L(\gamma)=\int d\gamma,$$

where $\gamma$ is the cross-section curve, and $L(\gamma)$ is the perimeter. The estimated body measurements 26 output 110 by the 3D model matching module 22 may comprise chest volume, waist volume, hip volume, front shoulders, front chest, front waist, front hips, shoulder to waist length, sleeve length, body length, leg length, outside leg length, and inside leg length.

It will be appreciated that there are a variety of different configurations for the body measurement systems and methods disclosed herein. Accordingly, it will be appreciated that the configurations illustrated in FIGS. 1 through 12 are provided for illustration and explanation only, and are not meant to be limiting. It will be appreciated that implementations of the disclosed embodiments and the functional operations described herein can be integrated or combined. The algorithms described herein can be executed by one or more processors operating pursuant to instructions stored on a tangible, non-transitory computer-readable medium. Examples of the computer-readable medium include optical media, magnetic media, semiconductor memory devices (e.g., EPROM, EEPROM, etc.), and other electronically readable media such as random or serial access devices, flash storage devices and memory devices (e.g., RAM and ROM). The computer-readable media may be local to the computers, processors, and/or servers executing the instructions, or may be remote such as when coupled via a computer network or cloud-based network, such as the Internet.

The algorithms and functional operations described herein can be implemented as one or more software modules executed by one or more processors, firmware, digital electronic circuitry, and/or one or more hardware modules such as application specific integrated circuits (ASICs) or other types of programmable hardware such as gate arrays. The functions of single devices described herein can be separated into multiple units, or the functions of multiple units can be combined into a single unit such as a System on Chip (SoC). Unless otherwise specified, the algorithms and functional operations described herein can be implemented in hardware or software according to different design requirements. A computer capable of executing the algorithms and functional operations described herein can include, for example, general and/or special purposes microprocessors or any other kind of central processing unit. Such computers can be implemented to receive data from and/or transfer data to one or more data storage or other electronic devices, or data storage systems (e.g., cloud-based systems). Additionally, such computers can be integrated with other devices, for example, mobile devices (e.g., mobile phones, video and/or audio devices, storage devices, personal digital assistants (PDAs), laptops, etc.).

Although the foregoing has been described in some detail for purposes of clarity, it will be apparent that certain changes and modifications may be made without departing from the principles thereof. It should be noted that there are many alternative ways of implementing both the systems and methods described herein. Accordingly, the present embodiments are to be considered as illustrative and not restrictive, and the invention is not limited to the details given herein, but may be modified within the scope and equivalents of the disclosed embodiments.

What is claimed is:

1. A method for estimating body measurements of a subject, comprising:
   receiving at least two images containing the subject;
   generating landmark heatmap data from the at least two images containing the subject;
   relating the landmark heatmap data to an abstract three-dimensional body model to determine a shape of the subject's body,
   wherein relating the landmark heatmap data to the abstract three-dimensional body model to determine the shape of the subject's body comprises extracting a plurality of contour points from the landmark heatmap data, and wherein the plurality of contour points comprises at least one control point,
   generating the abstract three-dimensional body model using the plurality of contour points, wherein the abstract three-dimensional body model comprises a plurality of body slices, and wherein each slice of the plurality of body slices represents an anthropometric measurement of a body that influences body shape,
   projecting each body slice of the plurality of body slices as a corresponding two-dimensional landmark,
   generating at least one main cross-section value by matching the at least one control point to the corresponding two-dimensional landmark, wherein the at least one main cross-section value is used to construct a cross-section curve,
   extracting a vertex from the cross-section curve, and constructing a surface of a part of the subject's body using the vertex from the cross-section curve; and
   estimating the body measurements of the subject based on the shape of the subject's body.

2. The method of claim 1, wherein the at least two images containing the subject are generated from a digital imaging device.

3. The method of claim 2, wherein the digital imaging device comprises a mobile device camera.

4. The method of claim 1, wherein the landmark heatmap data is generated using an intelligent computing system.

5. The method of claim 4, wherein the intelligent computing system comprises a trained neural network.

6. The method of claim 1, wherein generating the landmark heatmap data from the at least two images containing the subject comprises:
   generating a first portion of the landmark heatmap data using a first intelligent computing system, wherein the first intelligent computing system is trained to analyze front-view photographic images, wherein one of the at least two images containing the subject is a front-view image containing the subject, and wherein the first intelligent computing system analyzes the front-view image containing the subject to generate the first portion of the landmark heatmap data; and
   generating a second portion of the landmark heatmap data using a second intelligent computing system, wherein the second intelligent computing system is trained to analyze side-view photographic images, wherein another of the at least two images containing the subject is a side-view image containing the subject, and wherein the second intelligent computing system analyzes the side-view image containing the subject to generate the second portion of the landmark heatmap data.

7. The method of claim 6, wherein generating the first portion of the landmark heatmap data using the first intelligent computing system comprises:
   computing two-dimensional probability map distribution data using the front-view image containing the subject, wherein the two-dimensional probability map distribution data represents the probability that a pixel is associated with a part of the subject's body; and
   calculating a two-dimensional coordinate value $(x_i, y_i)$ for a keypoint i using the formula:

$$x_i, y_i = \mathrm{argmax}(H_i),$$

where, $H_i$ is a two-dimensional probability map of the i-th keypoint, wherein the i-th keypoint represents an area in the front-view image containing the subject where the part of the subject's body may be located.

8. The method of claim 6, wherein generating the second portion of the landmark heatmap data using the second intelligent computing system comprises:
   computing two-dimensional probability map distribution data using the side-view image containing the subject, wherein the two-dimensional probability map distribution data represents the probability that a pixel is associated with a part of the subject's body; and
   calculating a two-dimensional coordinate value $(x_i, y_i)$ for a keypoint i using the formula:

$$x_i, y_i = \mathrm{argmax}(H_i),$$

where, $H_i$ is a two-dimensional probability map of the i-th keypoint, wherein the i-th keypoint represents an area in the side-view image containing the subject where the part of the subject's body may be located.

9. The method of claim 6, wherein the first intelligent computing system and the second intelligent computing system each comprise a trained neural network.

10. The method of claim 1, wherein projecting each body slice of the plurality of body slices as the two-dimensional landmark comprises using a virtual camera to project each body slice of the plurality of body slices as the two-dimensional landmark.

11. The method of claim 10, further comprising:
    proportionally aligning a scale of the three-dimensional body model relative to the virtual camera used to project each body slice of the plurality of body slices, wherein a height of the subject is used to proportionally align the scale of the three-dimensional body model relative to the virtual camera.

12. The method of claim 1, further comprising:
    approximating the plurality of body slices using B-spline curves.

13. The method of claim 12, wherein the plurality of body slices is constructed as linear combinations of the B-spline curves and the at least one control point using the formula:

$$C(t) = \Sigma_{i=0}^{n} N_{i,p}(t) \cdot (P_i)$$

where basis functions are described using a recursion formula:

$$N_{i,0}(t) = \begin{cases} 1, t_i \leq t \leq t_{i+1} \\ 0, \text{in other case} \end{cases}$$

$$N_{i,j}(t) = \frac{t - t_i}{t_{i+j} - t_i} \cdot N_{i,j-1}(t) + \frac{t_{i+j+1} - t}{t_{i+j+1} - t_{i+1}} \cdot N_{i+j+1(t)}; j = 1, p.$$

14. The method of claim 13, wherein the recursion formula comprises a Cox de Boor recursion formula.

15. The method of claim 1, wherein estimating the body measurements of the subject based on the shape of the subject's body comprises:
calculating a perimeter of the cross-section curve using a curvilinear integral formula:

$$L(\gamma) = \int d\gamma,$$

where $\gamma$ is the cross-section curve, and $L(\gamma)$ is the perimeter.

16. The method of claim 1, wherein the body measurements of the subject comprise chest volume, waist volume, hip volume, front shoulders, front chest, front waist, front hips, shoulder-to-waist length, sleeve length, body length, leg length, outside leg length, and inside leg length.

17. The method of claim 1, further comprising:
detecting quality criteria of at least one of the at least two images containing the subject to determine whether the at least one of the at least two images containing the subject meets pre-defined quality standards.

18. The method of claim 17, wherein detecting the quality criteria of the at least one of the at least two images containing the subject comprises:
generating segment heatmap data from the at least one of the at least two images containing the subject;
generating mask heatmap data from the at least one of the at least two images containing the subject;
extracting features from the landmark heatmap data of the at least one of the at least two images containing the subject; and
analyzing the features extracted from the landmark heatmap data to determine whether the at least one of the at least two images satisfies a first pre-defined criterion.

19. The method of claim 18, wherein the features extracted from the landmark heatmap data comprise number of zero landmarks, landmark spread, and landmark max.

20. The method of claim 19, wherein the first pre-defined criterion comprises the number of zero landmarks equals zero.

21. The method of claim 18, further comprising:
extracting features from the segment heatmap data of the at least one of the at least two images containing the subject;
extracting features from the mask heatmap data of the at least one of the at least two images containing the subject;
analyzing the features extracted from the segment heatmap data; and
analyzing the features extracted from the mask heatmap data.

22. The method of claim 21, wherein the features extracted from the segment heatmap data comprise segment quality, segment max, segment poles, and number of zero segments.

23. The method of claim 21, wherein the features extracted from the mask heatmap data comprise mask quality.

24. A system for estimating body measurements of a subject, comprising:
at least one server capable of storing or processing, or both storing and processing a plurality of photographic images of a subject;
at least one intelligent computing system coupled to the at least one server, wherein the at least one intelligent computing system capable of analyzing the plurality of photographic images of the subject to generate landmark heatmap, contour segment heatmap data, and mask heatmap data; and
a module capable of relating the landmark heatmap data to an abstract three-dimensional body model to determine a shape of the subject's body and estimating body measurements of the subject based on at least the landmark heatmap data,
wherein the abstract three-dimensional body model is generated using a plurality of contour points, and wherein the plurality of contour points is extracted from the landmark heatmap data, and the plurality of contour points comprises at least one control point,
wherein the abstract three-dimensional body model comprises a plurality of body slices and each slice of the plurality of body slices represents an anthropometric measurement of a body that influences body shape,
wherein each body slice of the plurality of body slices is projected as a corresponding two-dimensional landmark,
wherein at least one main cross-section value is generated by matching the at least one control point to the corresponding two-dimensional landmark, and wherein the at least one main cross-section value is used to construct a cross-section curve,
wherein a vertex is extracted from the cross-section curve, and
wherein a surface of a part of the subject's body is constructed using the vertex from the cross-section curve.

25. The system of claim 24, further comprising:
at least one detector coupled to the least one intelligent computing system, the at least one detector capable of detecting quality of the plurality of photographic images based on the landmark heatmap data, the contour segment heatmap data, and the mask heatmap data.

26. The system of claim 24, wherein the at least one intelligent computing system is a trained neural network.

* * * * *